United States Patent
Plumptre et al.

(10) Patent No.: US 10,413,678 B2
(45) Date of Patent: *Sep. 17, 2019

(54) ASSEMBLY AND INDICATOR FOR A DRUG DELIVERY DEVICE

(71) Applicant: SANOFI-AVENTIS DEUTSCHLAND GMBH, Frankfurt am Main (DE)

(72) Inventors: David Plumptre, Worcestershire (GB); Warren Terry, Warwick (GB); Robert Veasey, Warwickshire (GB); Matthew Jones, Warwickshire (GB); Timothy Giles Claughton, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/340,037

(22) Filed: Nov. 1, 2016

(65) Prior Publication Data
US 2017/0043099 A1 Feb. 16, 2017

Related U.S. Application Data

(63) Continuation of application No. 13/392,882, filed as application No. PCT/EP2010/063842 on Sep. 21, 2010, now Pat. No. 9,511,193.

(30) Foreign Application Priority Data

Sep. 23, 2009 (EP) ...................... 09171134

(51) Int. Cl.
*A61M 5/315* (2006.01)
*A61M 5/31* (2006.01)

(52) U.S. Cl.
CPC ...... *A61M 5/31585* (2013.01); *A61M 5/3146* (2013.01); *A61M 5/31555* (2013.01);
(Continued)

(58) Field of Classification Search
CPC .... A61M 5/14248; A61M 2005/14252; A61M 2005/14268; A61M 5/31555;
(Continued)

(56) References Cited

U.S. PATENT DOCUMENTS 533,575 A 2/1895 Wilkens
3,905,366 A * 9/1975 Callahan ........... A61M 5/31525
604/209

(Continued)

FOREIGN PATENT DOCUMENTS

EP 0937471 A2 8/1999
EP 0937476 A2 8/1999
(Continued)

OTHER PUBLICATIONS

Form PCT/IB/326, Notification Concerning Transmittal of International Preliminary Report on Patentability.

*Primary Examiner* — Brandy S Lee
(74) *Attorney, Agent, or Firm* — Fish & Richardson P.C.

(57) ABSTRACT

An assembly for a drug delivery device, comprising a housing having a proximal end and a distal end, a piston rod and an indicator. The piston rod is adapted to be displaced distally with respect to the housing away from a proximal start position and towards a distal end position for delivering a drug. The indicator is adapted for indicating at least two different operation conditions of the assembly, the indicator being moveable with respect to the housing from a first indication position for a first condition of the assembly into a second indication position for a second condition of the assembly. The piston rod and the indicator are configured to mechanically interact for converting movement of the piston rod into movement of the indicator. A first detent is provided which is configured to releasably secure the indicator in the first indication position such that movement into the second indication position is allowed. A second detent is provided (Continued)

which is configured to secure the indicator in the second indication position such that movement into the first indication position is prevented.

16 Claims, 6 Drawing Sheets

(52) U.S. Cl.
CPC . *A61M 5/31593* (2013.01); *A61M 2005/3125* (2013.01); *A61M 2205/584* (2013.01)

(58) Field of Classification Search
CPC .... A61M 2005/3125; A61M 2205/584; A61M 5/3146; A61M 5/31585; A61M 5/31593
See application file for complete search history.

(56) References Cited

U.S. PATENT DOCUMENTS

| | | | |
|---|---|---|---|
| 4,973,318 A * | 11/1990 | Holm | A61M 5/24 604/208 |
| 5,042,977 A | 8/1991 | Bechtold et al. | |
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,030,363 A | 2/2000 | Kriesel | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,770,056 B2 * | 8/2004 | Price | G01F 11/023 222/43 |
| 6,899,698 B2 | 5/2005 | Sams | |
| 6,936,032 B1 | 8/2005 | Bush, Jr. et al. | |
| 7,104,972 B2 | 9/2006 | Moller et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0112299 A1 | 5/2007 | Smit et al. | |
| 2007/0194976 A1 | 8/2007 | Jacobs et al. | |
| 2008/0051713 A1 | 2/2008 | Kohlbrenner et al. | |
| 2008/0228143 A1 | 9/2008 | Stamp | |
| 2009/0275916 A1 | 11/2009 | Harms et al. | |

FOREIGN PATENT DOCUMENTS

| | | |
|---|---|---|
| JP | 2007-289741 | 11/2007 |
| WO | WO 98/10814 | 3/1998 |
| WO | 9938554 A1 | 8/1999 |
| WO | 0110484 A1 | 2/2001 |
| WO | 2008/031238 | 3/2008 |
| WO | 2008/154616 | 12/2008 |

* cited by examiner

ASSEMBLY AND INDICATOR FOR A DRUG DELIVERY DEVICE

CROSS REFERENCE TO RELATED APPLICATIONS

The present application is a continuation of U.S. patent application Ser. No. 13/392,882, filed Jul. 14, 2012, which is a U.S. National Phase Application pursuant to 35 U.S.C. § 371 of International Application No. PCT/EP2010/063842 filed Sep. 21, 2010, which claims priority to European Patent Application No. 09171134.0 filed Sep. 23, 2009. The entire disclosure contents of these applications are herewith incorporated by reference into the present application.

TECHNICAL FIELD

This disclosure relates to an assembly for a drug delivery device. Furthermore, the disclosure relates to an indicator for a drug delivery device.

BACKGROUND

In a drug delivery device, often, a bung within a cartridge containing a plurality of doses of a drug is displaced with respect to the cartridge in a distal direction by a piston rod. Thereby, a dose of the drug may be expelled from the cartridge.

Drug delivery devices are described in documents WO 2008/031238 A1 and US 2007/0197976 A1, for example.

SUMMARY

It is an object of the present disclosure to provide an assembly and an indicator facilitating provision of a novel, preferably an improved, drug delivery device.

This object may be achieved by the subject matter of the independent claims. Further features and advantageous embodiments are the subject matter of the dependent claims.

According to one aspect, an assembly for a drug delivery device is provided. The assembly may comprise a housing. The housing may have a proximal end and a distal end. The assembly may comprise a piston rod. The piston rod may be adapted to be displaced distally with respect to the housing away from a proximal start position and towards a distal end position for delivering a drug. The assembly may comprise an indicator. The indicator may be adapted to indicate at least two different operation conditions of the assembly. The indicator may be moveable with respect to the housing from a first indication position for a first condition, e.g. an unprimed condition, of the assembly into a second indication position for a second condition, e.g. a primed condition, of the assembly. The piston rod and the indicator may be configured to mechanically interact for converting movement, preferably rotational movement, of the piston rod into movement, preferably rotational movement, of the indicator.

The assembly may comprise a first detent. The first detent may be configured to releasably secure the indicator in the first indication position such that movement into the second indication position is allowed. The assembly may comprise a second detent. The second detent may be configured to secure the indicator in the second indication position such that movement into the first indication position is prevented.

A further aspect relates to an indicator for a drug delivery device. The indicator may comprise an inner member. The indicator may comprise an outer indication element. The outer indication element may provide an indication surface. The outer indication element may be resiliently connected to the inner member by at least one flexible member.

A further aspect relates to an indicator for a drug delivery device. The indicator may comprise an inner member. The indicator may comprise an outer indication element. The outer indication element may provide an indication surface. The outer indication element may be resiliently connected to the inner member by at least one flexible member. The indicator may comprise at least one first detent. The indicator may comprise at least one second detent. The first detent may be adapted to enable rotation of the indicator in a first direction. The second detent may be adapted to prevent rotation of the indicator in the direction opposite to the first direction.

The drug delivery device expediently comprises the assembly described above. The drug delivery device may comprise a cartridge holding a drug. The drug may be a liquid medication, comprising for example GLP-1, long-acting or short-acting insulin, heparin or growth hormones. A bung may be retained in the cartridge. The bung may seal the cartridge proximally. The drug delivery device may be an injection device. The drug delivery device may be a pen-type device, e.g. a pen-type injector.

The drug delivery device and the housing have a distal end and a proximal end. The term "distal end" designates that end of the drug delivery device or a component thereof which is or is to be arranged closest to a dispensing end of the drug delivery device. The term "proximal end" designates that end of the device or a component thereof which is or is to be arranged furthest away from the dispensing end of the device.

According to an embodiment, the indicator is configured to be a prime status indicator. The first indication position may denote an unprimed condition of the device. The second indication position may denote a primed condition of the device.

When the device is unprimed, there may be a gap between the piston rod and the bung. The gap may arise from manufacturing or assembly tolerances. When delivering the drug, the gap may reduce the dose accuracy. Thus, a user may dispense an underdose, which may have fatal or lethal consequences.

In order to reduce, in particular to remove, the gap, the device may be primed. Thereby, a minimum dose of the drug, e.g. a prime dose, may be set and dispensed from the cartridge. The indicator may be driven, in particular rotated, by the piston rod when the device is primed, e.g. when the device is switched from the unprimed condition into the primed condition. Due to rotational movement of the indicator, the indicator is switched from the first indication position, e.g. an unprimed position, into the second indication position, e.g. a primed position. When the indicator is in the primed position, the user is indicated, that the device was primed. In this way, a user-friendly drug delivery device is achieved, providing high safety for the user. After priming the device, a first dose of the drug can be set and delivered to the user.

According to an embodiment, the second detent irreleasably secures the indicator in the second indication position while the piston rod travels to the distal end position.

Preferably, the indicator is releasably secured in the first indication position by means of the first detent. Preferably, the indicator is irreleasably kept in the second indication position by means of the second detent. Preferably, the second detent prevents rotation of the indicator back into the first indication position once the device has been primed. Hence, the indicator may stay in the primed position once the device was primed. In this way, dispensing of an additional prime dose and, hence, waste of a dose of the drug, may be prevented. Preferably, the indicator comprises the first detent and the second detent. The first detent and the second detent may comprise or may be embodied as a respective indentation.

According to an embodiment, the piston rod is rotatable in a first rotational direction with respect to the housing. The indicator may be arranged and configured to mechanically interact with the piston rod such that the indicator is at least partly rotated together with the piston rod in the first rotational direction when the assembly switches from the first indication position into the second indication position.

Preferably, the first rotational direction is a delivery direction. The delivery direction may be counter-clockwise, for example. The piston rod may drive the indicator in the delivery direction for switching the indicator from the first indication position into the second indication position when the device is primed. In this way, provision of an effective and easily handled drug delivery device is achieved.

According to an embodiment, the first detent comprises a ramp. The ramp may be adapted to releasably secure the indicator in the first indication position. The ramp may rise in the first rotational direction.

Preferably, the ramp reduces the torque needed to rotate the indicator in the delivery direction for switching the indicator from the first indication position into the second indication position. In this way, the force required for rotation of the indicator is reduced and, hence, provision of a user-friendly drug delivery device is facilitated.

According to an embodiment, a drive member is provided. A dose button may be provided. The dose button may be moveable with respect to the housing. Movement of the dose button may be converted into movement of the drive member by mechanical interaction of dose button and drive member. Movement of the dose button in the distal direction with respect to the housing may cause transition of the indicator from the first indication position into the second indication position.

For dispensing the prime dose, the user may move the dose button distally with respect to the housing. Movement of the dose button may be converted into rotational movement of the indicator for switching the indicator in the second indication position. In this way, an easily handled drug delivery device is achieved. Additional steps required for indicating the operational configuration of the device may be redundant.

According to an embodiment, at least one counter element is provided. The counter element may be configured to engage the respective detent. Preferably, the at least one counter element is part of the drive member. When the counter element engages with one of the detents, the counter element may be disengaged from the other one of the detents.

The counter element may be a protrusion. Preferably, when the device is unprimed, the counter element engages, preferably releasably engages, with the first detent. Releasable engagement may enable rotation of the indicator towards the second indication position when the device is primed. After the device was primed, the counter element may engage, preferably irreleasably engage, with the second detent. In this way, rotation of the indicator from the second indication position back into the first indication position may be effectively prevented.

According to an embodiment, the indicator comprises an inner member. The indicator may comprise an outer indication element. The inner member and the outer indication element may be resiliently connected with each other such that the outer indication element is moveable with respect to the inner member when switching from the first indication position into the second indication position.

Preferably, the outer indication element is moveable in the proximal direction with respect to the inner element when dispensing the prime dose. Preferably, the inner member is a central hub. Preferably, the outer indication element is an outer ring.

According to an embodiment, the inner member and the outer indication element are connected by means of at least one flexible member. When the first detent and the second detent are disengaged from the counter element, the flexible member provides a force which tends to displace the indicator element in the distal direction with respect to the housing.

For disengaging the counter element from the first detent when the indicator is rotated towards the second indication position, the flexible member may allow the outer indication element to rise slightly in the proximal direction with respect to the inner element. Thereby, the flexible member may be biased. The flexible member may force the outer indication element back in the distal direction with respect to the inner element, for engaging with the second detent after the device was primed. In this way, the flexible member provides a force pushing the second detent towards the counter element for effectively, irreleasably securing the indicator in the second indication position.

According to an embodiment, the flexible member is secured to an end face of the outer indication element. The flexible member may run in the radial direction with respect to the housing. The flexible member may be shaped s-like. This may help to increase flexibility of the flexible member and, hence, may reduce the force the user must apply to rotate the indicator, e.g. when priming the device.

According to an embodiment, the dose button comprises a plurality of protrusions arranged on an inner surface of the dose button. The protrusions may be configured to mechanically interact with the at least one flexible member such that movement of the indicator away from the second indication position and back towards the first indication position is prevented.

When an external force is applied to bring the counter element out of engagement with the second detent, the flexible member may abut the protrusions. In this way, the effective length over which the flexible member is bent may be reduced and, hence, proximal displacement of the outer indication element may be prevented. Hence, the indicator may be effectively prevented from switching from the second indication position back into the first indication position.

According to an embodiment, the inner member is configured to cooperate with the piston rod for switching from the first indication position into the second indication position. The inner member may comprise at least one first surface. Movement of the piston rod may be converted into movement of the indicator by mechanical cooperation of the first surface and the piston rod.

According to an embodiment, the inner member comprises at least one second surface. Mechanical cooperation of the second surface and the piston rod may keep the indicator in the first indication position.

According to an embodiment, the first surface protrudes radially outwardly from the inner member. The second surface may be arranged closer to a proximal end of the piston rod than the first surface. An angular distance between the second surface and the piston rod may be smaller than an angular distance between the first surface and the piston rod.

Preferably, the second surface mechanically interacts with the piston rod before the device is primed, e.g. in an initial state of the device where the piston rod is in the proximal start position. Due to mechanical cooperation of the second surface and the piston rod, unintentional rotation of the indicator towards the second indication position, in which the indicator indicates that the device was primed, may be prevented. Hence, erroneous indication of the primed condition of the device before the device was primed is prevented.

Preferably, the first surface mechanically interacts with the piston rod when the device is primed, in particular when delivering the prime dose. In this way, rotation of the piston rod may be effectively converted into rotation of the indicator for switching the indicator from the first indication position into the second indication position.

According to a preferred embodiment, an assembly for a drug delivery device is provided. The assembly comprises a housing having a proximal end and a distal end, a piston rod which is adapted to be displaced distally with respect to the housing away from a proximal start position and towards a distal end position for delivering a drug and an indicator for indicating at least two different operation conditions of the assembly. The indicator is moveable with respect to the housing from a first indication position for a first condition of the assembly into a second indication position for a second condition of the assembly. The piston rod and the indicator are configured to mechanically interact for converting movement of the piston rod into movement of the indicator. A first detent is provided which is configured to releasably secure the indicator in the first indication position such that movement into the second indication position is allowed, and a second detent is provided which is configured to secure the indicator in the second indication position such that movement into the first indication position is prevented.

The device, in particular the indicator, may provide clear visual signals indicating to the user whether the device is in the first condition, e.g. the unprimed condition, or in the second condition, e.g. the primed condition. As the signal is preferably binary, it may be very difficult to misinterpret it. Hence, a user-friendly and easily handled drug delivery device is achieved providing high safety for the user.

Of course, features described above in connection with different aspects and embodiments may be combined with each other and with features described below.

BRIEF DESCRIPTION OF THE FIGURES

Further features and refinements become apparent from the following description of the exemplary embodiments in connection with the accompanying figures.

DETAILED DESCRIPTION

Figure 1:
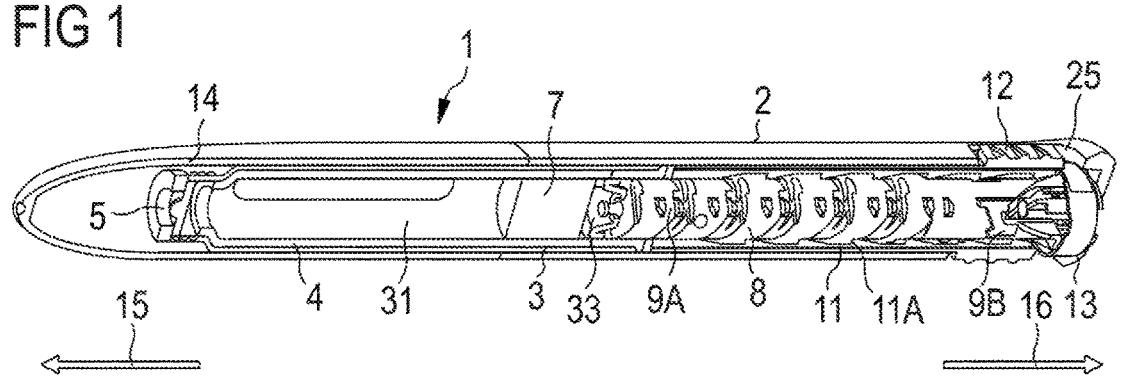
FIG. 1 schematically shows a perspective sectional view of an exemplary embodiment of a drug delivery device, FIG. 2 schematically shows a perspective sectional view of a part of the drug delivery device of FIG. 1, FIG. 3 schematically shows a perspective side view of a part of the drug delivery device of FIG. 2, FIG. 4 schematically shows a perspective sectional view of the part of the drug delivery device of FIG. 3, FIG. 5 schematically shows a perspective sectional view of a part of the drug delivery device of FIG. 1 in an unprimed condition, FIG. 6 schematically shows a perspective sectional view of a part of the drug delivery device of FIG. 1 in a primed condition, FIG. 7 schematically shows a perspective sectional view of a part of the drug delivery device of FIG. 1, FIG. 8 schematically shows a top view of the part of the drug delivery device of FIGS. 3 and 4, FIG. 9 schematically shows a perspective sectional view of a part of the drug delivery device of FIG. 1 while switching from the unprimed condition into the primed condition.

Like elements, elements of the same kind and identically acting elements may be provided with the same reference numerals in the figures.

In FIG. 1, a drug delivery device 1 is shown. The drug delivery device 1 comprises a cartridge holder 3. The device 1 comprises a cartridge 4. The cartridge 4 is retained in the cartridge holder 3. The cartridge holder 3 stabilizes the cartridge 4 mechanically.

The cartridge 4 holds a plurality of doses of a drug 31. The drug 31 is preferably a liquid medication, comprising, for example, GLP-1, insulin, like short-acting or long-acting insulin, heparin or growth hormones. The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 4 has an outlet 5. The drug 31 can be dispensed from the cartridge 4 through the outlet 5. The device 1 comprises a cap 14 which protects the cartridge 4 against external influences.

The drug delivery device 1 may be an injection device. The drug delivery device 1 may be a pen-type device, in particular a pen-type injector. The device 1 may be a disposable or a re-usable device. Preferably, the device 1 is a fixed dose device, in particular a device configured to dispense doses of the drug 31 which may not be varied by the user. Alternatively, the device 1 may be configured to dispense variable, preferably user-settable, doses of the drug 31. The drug delivery device 1 may be a manually, in particular a non-electrically, driven device.

The drug delivery device 1 comprises a housing 2. The drug delivery device 1 and the housing 2 have a distal end and a proximal end. The term "distal end" designates that end of the drug delivery device 1 or a component thereof which is or is to be arranged closest to a dispensing end of the drug delivery device 1. The distal end of the device 1 is indicated by arrow 15. The term "proximal end" designates that end of the device 1 or a component thereof which is or is to be arranged furthest away from the dispensing end of the device 1. The proximal end of the device 1 is indicated by arrow 16.

The drug delivery device 1 comprises a bung 7. The bung 7 is retained in the cartridge 4. The bung 7 is moveable with respect to the cartridge 4. The bung 7 seals the cartridge 4 proximally. Movement of the bung 7 in the distal direction with respect to the cartridge 4 causes the drug 31 to be dispensed from the cartridge 4 through the outlet 5.

The device 1 comprises a piston rod 8. The piston rod 8 operates through the housing 2 of the drug delivery device 1. The piston rod 8 is rotatable in a delivery direction with respect to the housing 8 for delivering a dose. The piston rod 8 is designed to transfer axial movement through the drug delivery device 1, for example for the purpose of dispensing the drug 31. In particular, the piston rod 8 is designed to transfer force to the bung 7, thereby pushing the bung 7 in the distal direction with respect to the cartridge 4. In this way, a dose of the drug 31 is dispensed from the cartridge 4. The size of the dispensed dose is determined by the distance by which the bung 7 is displaced in the distal direction with respect to the cartridge 4.

The device 1 comprises a drive mechanism. The drive mechanism is arranged within the housing 2 of the drug delivery device 1. The drive mechanism comprises a dose button 12. The dose button 12 may comprise or may be embodied as a sleeve. The dose button 12 is moveable with respect to the housing 2. Preferably, the dose button 12 is splined to the housing 2. The dose button 12 is moveable in the proximal direction with respect to the housing 2 for setting a dose of the drug 31. The dose button 12 is moveable in the distal direction with respect to the housing 2 for delivering the dose of the drug 31.

The distance by which the dose button 12 is moved proximally with respect to the housing 2 for setting the dose of the drug 31 may determine the size of the dose. A proximal end position and a distal end position of the dose button 12 with respect to the housing 2 is determined by a respective stop feature (not explicitly shown) limiting the proximal or distal movement of the dose button 12 with respect to the housing 2.

The drive mechanism comprises a drive member 11. The drive member 11 may comprise or may be embodied as a sleeve. The drive member 11 is axially moveable with respect to the housing 2. The drive member 11 is prevented from rotating with respect to the housing 11. The drive member 11 is secured against movement with respect to the dose button 12. Axial movement of the dose button 12 is converted into axial movement of the drive member 11 with respect to the housing 2.

Figure 9:
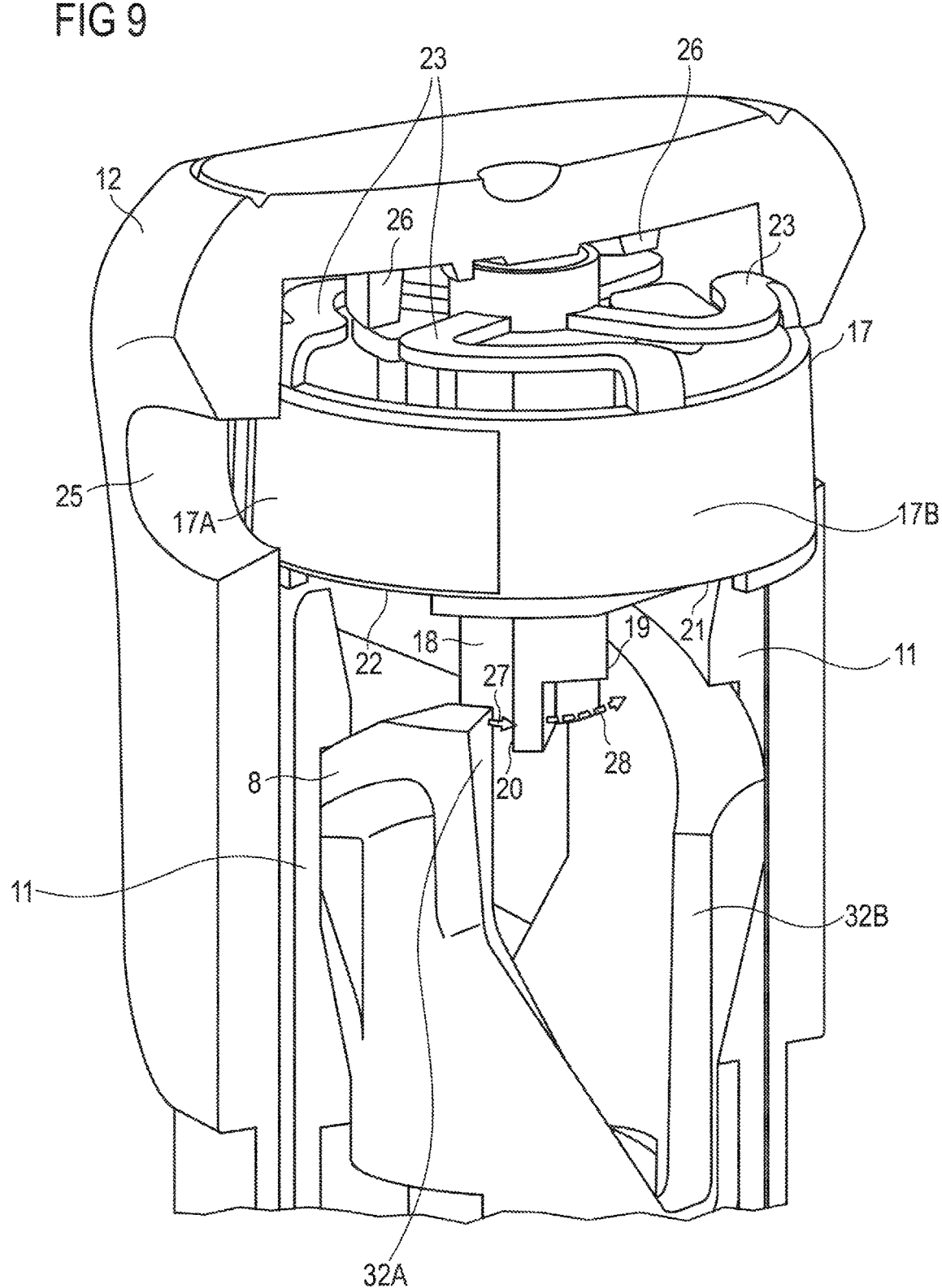

A user-applied force causing the dose button 12 to be moved distally with respect to the housing 2 is transferred to the piston rod 8 by the drive mechanism for dispensing the dose (see FIGS. 1 and 9). The piston rod 8 comprises a thread 9B. Thread 9B is arranged in the proximal end section of the piston rod 8. Thread 9B is formed on flexible arms of the piston rod 8 (see arms 32A, 32B in FIG. 9). The drive member 11 comprises a mating thread 11A. Thread 11A is arranged at an inner surface of the drive member 11. Thread 11A comprises a ramp on one side. Due to mechanical cooperation of thread 9B and mating thread 11A axial movement of the drive member 11 is converted into rotation of the piston rod 8 in the delivery direction for dispensing a dose of the drug 31. The rotation axis is a main longitudinal axis of the housing 2 or the device 1. Preferably, the rotation axis runs along the piston rod 8 and, in particular, along a main direction of extent of the piston rod 8.

The piston rod 8 comprises a further thread 9A. Due to mechanical cooperation of thread 9A and a mating thread of a further component of the drive mechanism (not explicitly shown), the piston rod 8 travels in the distal direction with respect to the housing 2 for dispensing the dose of the drug 31. Thereby, from dispensing of a prime dose, which is explained later on in more detail, to dispensing of a last dose of the drug 31 held in the cartridge 4, the piston rod 8 travels distally with respect to the housing 2 away from a proximal start position and towards a distal end position for delivering the drug 31.

In an initial state of the device 1, e.g. an unprimed condition of the device 1, there is a gap 33 between the piston rod 8 and the bung 7, as indicated in FIG. 1. The gap 33 arises from manufacturing or assembly tolerances. The size of the gap 33 may vary. However, when delivering the drug 31, the gap 33 between the piston rod 8 and the bung 7 reduces the dose accuracy, because the piston rod 8 has to close the gap 33 before the bung 7 is advanced and drug 31 is expelled.

In order to reduce, in particular to remove, the gap 33, the device 1 has to be primed. For priming the device 1, often, a minimum dose of the drug 31, e.g. a prime dose, is set and dispensed from the cartridge 4. While dispensing the prime dose, the distance between the piston rod 8 and the bung 7 is removed and a small amount of the drug 31 is delivered from the cartridge 4. Afterwards, the piston rod 8 abuts the bung 7, i.e. the gap 33 between the piston rod 8 and the bung 7 was removed. After having removed the gap 33, the device 1 is ready for setting and delivering a first dose of the drug 31 to the user.

Often, it is difficult for the user to realize whether the device 1 was primed or not, i.e. whether the device 1 is ready to deliver the first dose. However, it is crucial for the user to know whether the device 1 has been primed or not, as if the user erroneously primes the device 1 although its has already been primed, the user may waste a dose of the drug 31. On the other hand, if the user dispenses the first dose, believing that the device 1 has already been primed, he may inject an underdose, which may have fatal, or even lethal consequences for the user.

Figure 2:
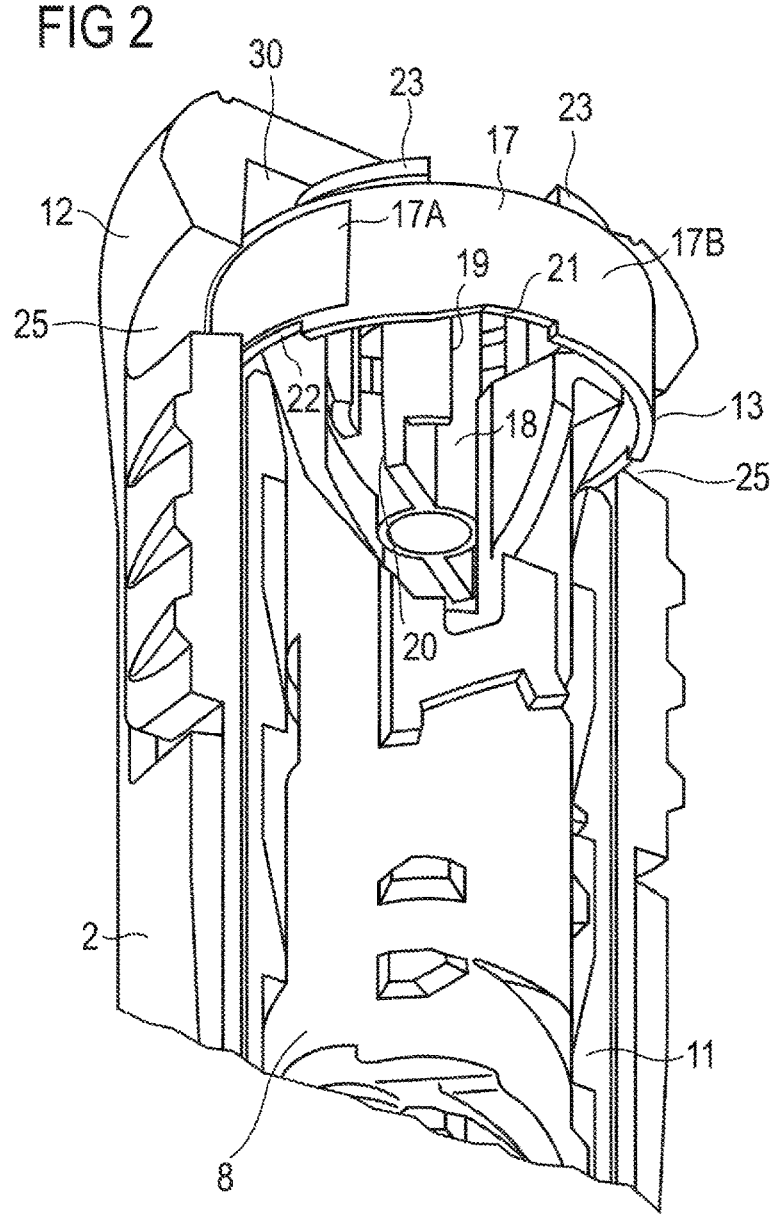
Figure 3:
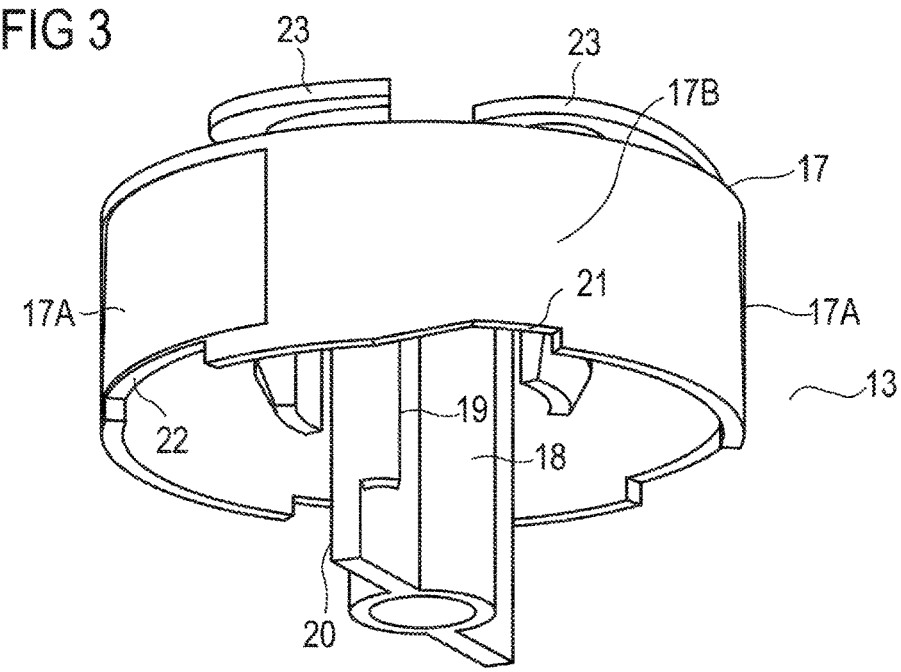
Figure 4:
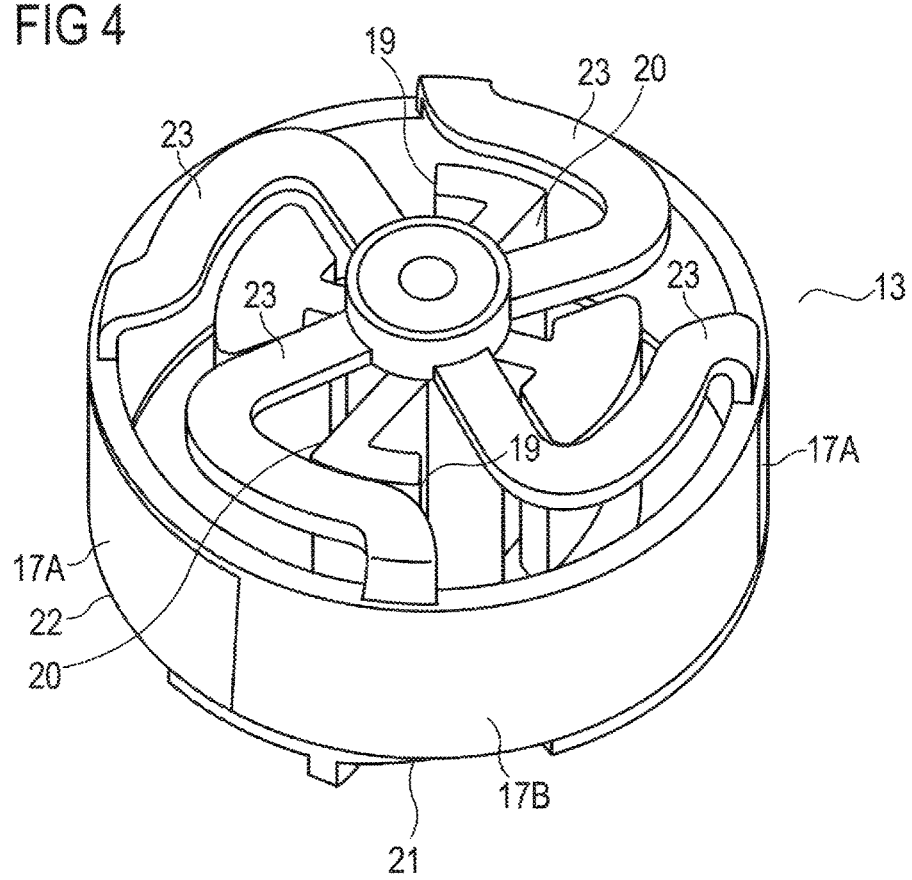

In order to distinguish the primed device 1, which is ready for setting and delivering the first dose to the user, from the unprimed device 1, e.g. in order to indicate if the prime dose has been dispended or not, the device 1 comprises an indicator 13 (see in particular FIGS. 2 to 4). The indicator 13 is a prime status indicator. The indicator 13 is adapted to indicate two different operation conditions, namely the primed condition (see FIG. 6) and the unprimed condition (see FIG. 5), of the device 1.

The indicator 13 is arranged in the proximal end section of the device 1. The indicator 13 is retained in the dose button 12. The indicator 13 is rotatable with respect to the dose button 12 in a limited fashion. The indicator 13 is secured against proximal displacement with respect to the dose button 12 and, hence, with respect to the drive member 11, by means of mechanical cooperation, in particular abutment, of a proximal end face of the indicator 13 with a proximal inner face 30 of the dose button 12 (see FIG. 2).

The indicator 13 is secured against distal displacement with respect to the dose button 12 and, hence, with respect to the drive member 11, by mechanical cooperation, in particular abutment, of a distal end face of the indicator 13 with a proximal end face of the drive member 11.

The indicator 13 is configured to mechanically cooperate with the piston rod 8 when the device 1 is primed, in particular when the prime dose is dispensed. When the piston rod 8 is rotated in the delivery direction with respect to the housing 2 for dispensing the prime dose, the piston rod 8 interacts with the indicator 13 such that the indicator 13 follows, in a limited fashion, rotation of the piston rod 8 in the delivery direction.

The indicator 13 comprises an inner member 18, as shown in FIG. 2, for example. The inner member 18 is adapted to cooperate with the piston rod 8. The indicator 13 comprises an outer indication element 17 (see FIG. 2 and also FIGS. 3 and 4). The outer indication element 17 is radially offset from the inner member 18. In particular, an outer surface, e.g. an indication surface 17A, 17B, of the outer indication element 17 is arranged closer to the inner surface of the dose button 12, than an outer surface of the inner member 18. The inner member 18 reaches further in the proximal direction with respect to the housing 2 than the outer indication element 17 in order to allow mechanical cooperation of the inner member 17 with the piston rod 8. The inner member 18 is partly arranged inside the outer indication element 17. The outer indication element 17 may comprise or may be embodied as an outer ring. The inner member 18 may comprise or may be embodied as a central hub.

Figure 5:
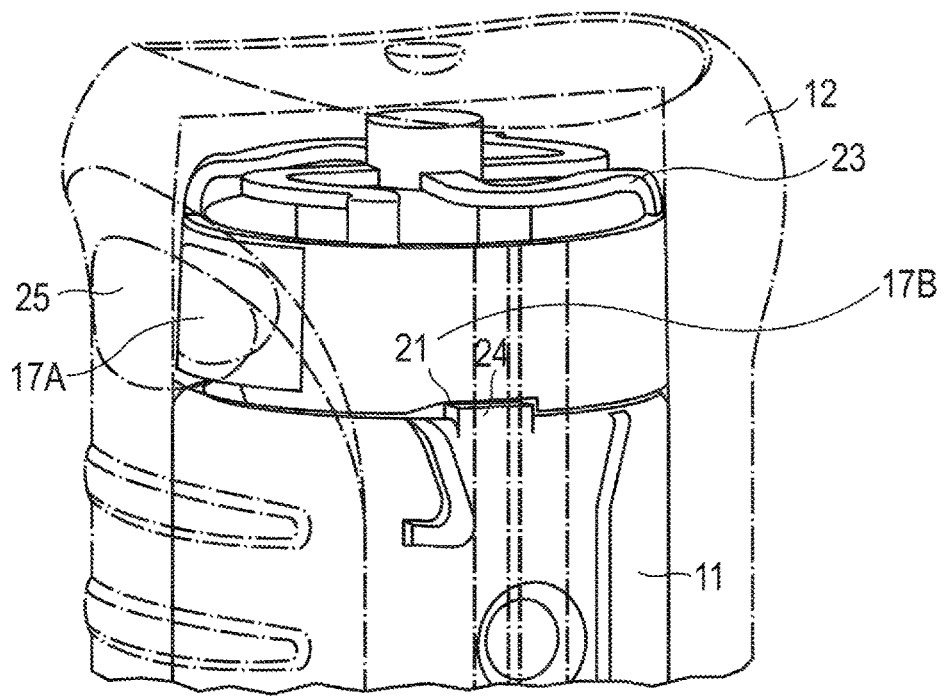
Figure 6:
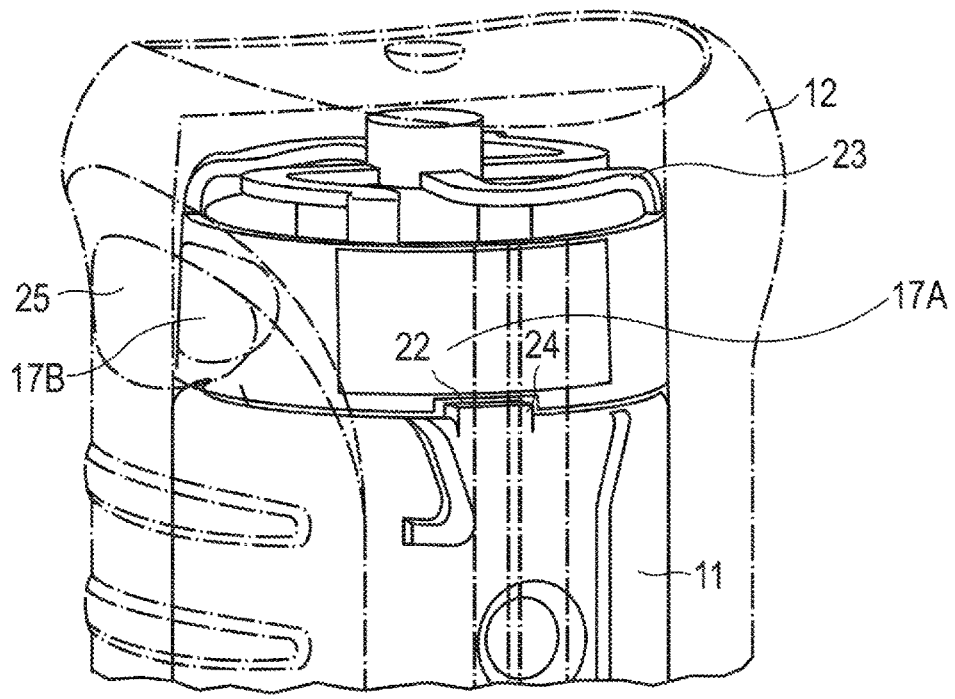

The outer indication element 17 is slightly axially moveable with respect to the inner member 18 while dispensing the prime dose, which is explained in connection with FIGS. 5 and 6 in more detail. The outer indication element 17 is resiliently connected to the inner member 18 by means of a plurality of flexible members 23 (see FIGS. 3 and 4). The respective flexible member 23 is a flexible web. The flexible members 23, the inner member 18 and the outer indication element 17 are formed unitarily.

The flexible members 23 are secured to the proximal end face of the outer indication element 17 and the inner member 18. In particular, the flexible members 23 resiliently connect the proximal end face of the inner member 18 with the proximal end face of the outer indication element 17. The flexible members 23 extend in the radial direction with respect to the housing 2. The flexible members 23 are shaped s-like. This may help to increase flexibility of the flexible members 23 and, hence, may reduce the force the user must apply to rotate the indicator 13, e.g. when priming the device 1. Hence, a user-friendly drug delivery device 1 is achieved.

When the device 1 is assembled, in particular when the dose button 12 is assembled over the indicator 13, the dose button 12 forces the inner member 18 in the distal direction with respect to the housing 2, thereby deforming the flexible members 23. This deformation tends to bias the outer indication element 17 in the distal direction with respect to the housing 2 and distally onto the drive member 11, which is explained later on in more detail.

The inner member 18 comprises a first interaction surface 20. The first interaction surface 20 is arranged in the distal end section of the inner member 18. The first interaction surface 20 protrudes radially outwardly from the inner member 18. The first interaction surface 20 and the inner member 18 are unitarily formed.

When the piston rod 8 is rotated for dispensing the prime dose, the piston rod 8, in particular the flexible arm 32A (see FIG. 9) of the piston rod 8, is moved towards the first interaction surface 20 until the flexible arm 32A abuts the first interaction surface 20. When the piston rod 8 is rotated further in the delivery direction with respect to the housing 2, the flexible arm 32A applies force onto the first interaction surface 20 and, hence, onto the indicator 13. Consequently, the piston rod 8 rotates the indicator 13 in the delivery direction with respect to the housing 2, thus switching the indicator 13 from a first indication position, e.g. the position of the indicator 13 when the device 1 is in the unprimed condition, into a second indication position, e.g. the position of the indicator 13 when the device 1 is in the primed condition.

For indicating the different operation conditions, e.g. the primed condition and the unprimed condition of the device 1, the outer indication element 17 provides two first indication surfaces 17A. The outer indication element 17 provides two second indication surfaces 17B. The respective indication surfaces 17A and 17B are different from each other. For example, the first indication surface 17A may comprise a different colour compared to the second indication surfaces 17A. Preferably, the first indication surfaces 17A comprise an orange or red colour for indicating that the device 1 is unprimed. The second indication surfaces 17A may comprise a green or white colour, for indicating that the device 1 has been primed.

The two first indication surfaces 17 are disposed oppositely. The two second indication surfaces 17B are disposed oppositely. The dose button 12 comprises two apertures 25. The two apertures 25 are disposed oppositely. The apertures 25 axially overlap with the outer indication element 17, in particular the respective indication surfaces 17A, 17B.

In the first indication position, e.g. when the device 1 is in the unprimed condition, a respective first indication surface 17A is visible through a respective aperture 25. When the indicator 13 and, hence, the outer indication element 17 was rotated into the second indication position, e.g. when the device 1 was switched into the primed condition due to dispensing the prime dose, a respective second interaction surface 17B is visible through a respective aperture 25. In this way, the user easily recognizes in which operation condition the device 1 is, irrespective of the position of the device 1 with respect to the user. Hence, a very user-friendly and safe drug delivery device 1 is achieved.

When the device 1 is unprimed, i.e. when the indicator 13 is in the first indication position, externally applied forces, such as those generated by vibration, impact or user tampering, may cause the indicator 13 to be unintentionally rotated into the second indication position such that the first indication surfaces 17A, e.g. the orange surfaces, move out of view and such that the user is erroneously indicated that the device 1 has been primed. In order to prevent that the indicator 13 is rotated in the second indication position without having primed the device, which may have fatal consequences for the user, the inner member 18 comprises a second interaction surface 19.

The second interaction surface 19 and the inner member 18 are formed unitarily. The second interaction surface 19 is part of a rib. The second interaction surface 19 is arranged closer to the proximal end section of the inner member 18 than the first interaction surface 20. This facilitates interaction of the piston rod 8 and the inner member 18, when the device 1 is in the initial state, i.e. when the piston rod 8 is in the proximal start position.

The second interaction surface 19 has a smaller angular distance with respect to the piston rod 8, in particular with respect to the flexible arm 32B of the piston rod 8 (see FIG.

Figure 8:
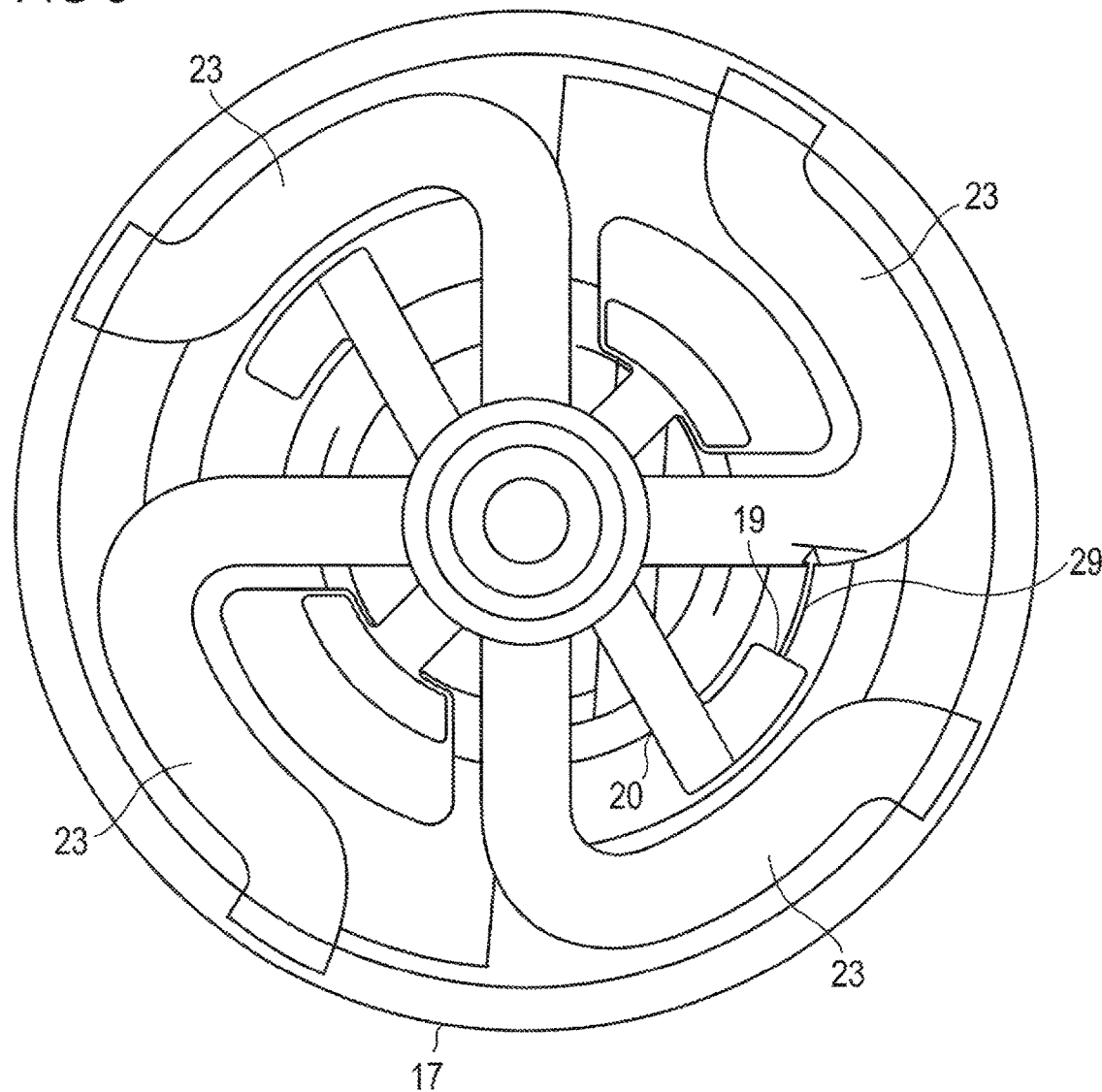

2 and, in particular, arrow 29 in FIG. 8), than the first interaction surface 20 has with respect to the flexible arm 32A when the device 1 is in the initial state. Preferably, the indicator 13 is splined to the piston rod 8 by mechanical cooperation of the second interaction surface 19 and the flexible arm 32B. Mechanical cooperation of the second interaction surface 19 and the flexible arm 32B prevents unintentional rotation of the indicator 13 and, hence, of the outer indication element 17 in the delivery direction and, hence, into the second indication position when the device 1 is in the initial state. In other words, the indicator 13 is kept in the first indication position by means of mechanical cooperation of interaction surface 19 and the piston rod 8. Furthermore, for keeping the indicator 13 in the first or in the second indication position, the outer indication element 17 comprises two first detents 21, as shown in FIG. 5. The respective first detent 21 is an indentation. The outer indication element 17 comprises two second detents 22, as shown in FIG. 6. The respective second detent 22 is an indentation. The respective detents 21, 22 are arranged at the distal end section of the outer indication element 17.

The two first detents 21 are disposed oppositely. The two second detents 22 are disposed oppositely. The first detents 21 and the second detents 22 are unitarily formed with the outer indication element 17. Preferably, the detents 21, 22 are moulded or milled into the outer indication element 17. The device 1 comprises two counter elements 24. The counter elements 24 are part of the drive member 11. The counter elements 24 are disposed oppositely. The drive member 11 and the counter elements 24 are unitarily formed. The respective counter element 24 is a protrusion, protruding from the drive member 11 in the proximal direction with respect to the housing 2.

The respective counter element 24 engages with one respective detent 21 or 22 for keeping the outer indication element 17 and, hence, the indicator 13 in one respective indication position. In other words, in the first indication position, e.g. in the unprimed position, the respective counter element 24 is engaged with the respective first detent 21. In the second indication position, e.g. in the primed position, the respective counter element 24 is engaged with the respective second detent 22. In particular, when the counter elements 24 are engaged with the first detents 21, the second detents 22 are disengaged and vice versa.

The first detents 21 comprise a ramp. The ramp rises in the rotational direction of the piston rod 8, i.e. the delivery direction. The ramp is adapted to releasably secure the indicator 13 in the first indication position. The ramp reduces the torque needed to rotate the indicator 13 in the delivery direction and out of engagement with the counter elements 24 while dispensing the prime dose. When the indicator 13 is rotated in the delivery direction, the counter elements 24 slide along the ramp, thus being brought out of engagement with the detents 21.

The flexible members 23 secured to the proximal end face of the indication element 17 allow the outer indication element 17 to ride up over the first detents 21. In other words, the flexible members 23 allow slight proximal movement of the outer indication element 17 for disengaging with the counter elements 24 while dispensing the prime dose, in particular while switching the indicator 13 from the first indication position into the second indication position. The flexible members 23 force the outer indication element 17, in particular the second detents 22, into cooperation with the counter elements 24 when the prime dose was dispensed.

The second detents 22 do not comprise a ramp but comprise side faces which run parallel to the main longitudinal axis of the housing 2. This helps to prevent rotation of the indicator 13 from the second indication position back into the first indication position. In this way, the second detents 22 facilitate irreleasably securing the indicator 13 in the second indication position while the piston rod 8 travels towards the distal end position when delivering the drug 31 to the user after the device 1 was primed.

Figure 7:
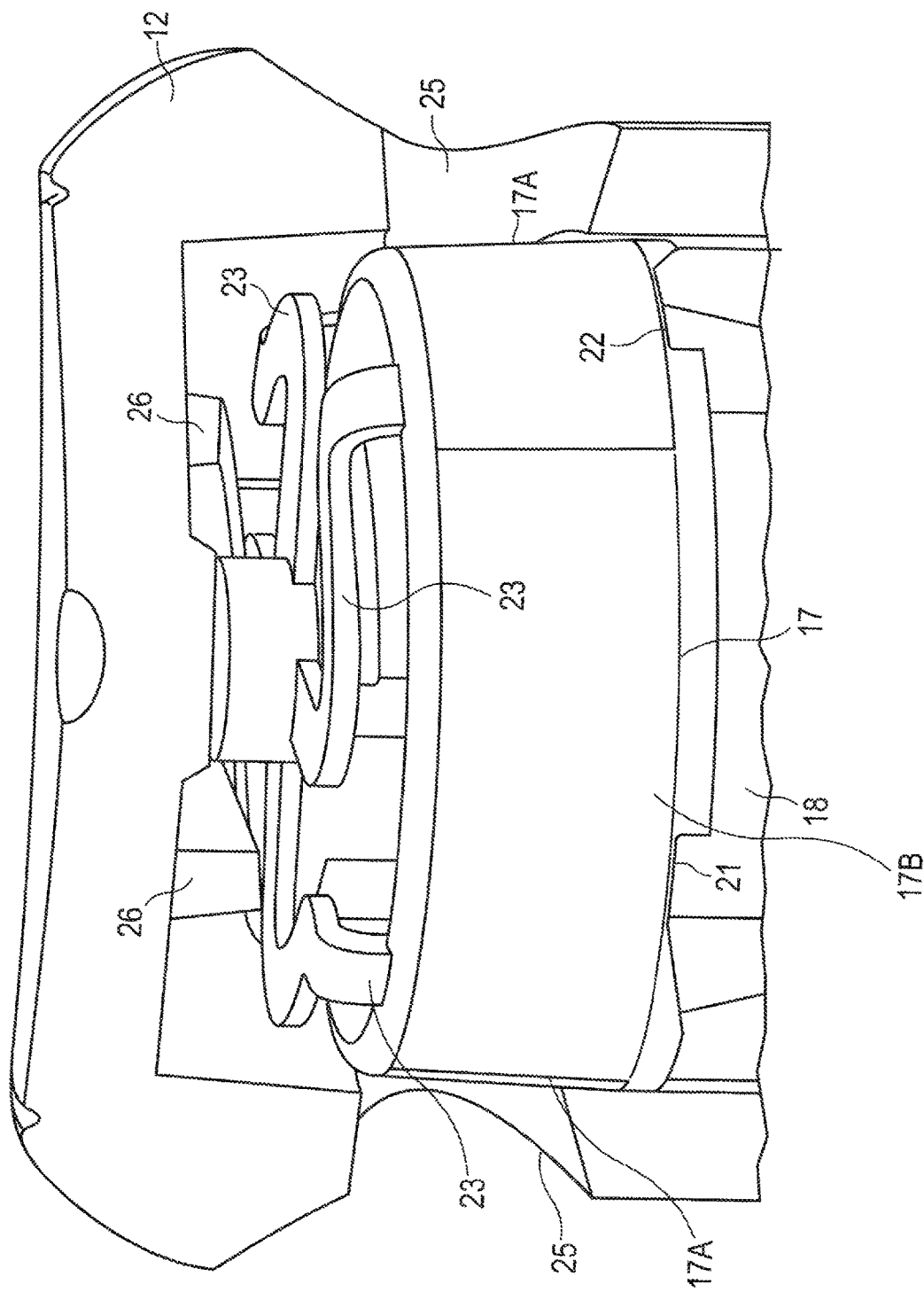

In order to help preventing movement of the indicator 13 from the second indication position back into the first indication position, the dose button 12 comprises a plurality of protrusions 26, which are indicated in FIG. 7. The protrusions are ramp-shaped, the ramps rising in the delivery direction. The protrusions 26 are arranged inside the dose button 12. The protrusions 26 are arranged at the proximal inner face 30 of the dose button 12. The protrusions 26 are axially aligned with the middle of outer surfaces of the flexible members 23 when the counter element 24 is engaged with the first detents 21 or with the second detents 22.

When an external force is applied to bring the counter element 24 out of engagement with the second detents 22, e.g. when the outer indication element 17 is slightly displaced proximally with respect to the inner member 18, the middle of the flexible members 23 abuts the protrusions 26. In this way, the effective length over which the flexible members 23 are bent is reduced and, hence, proximal displacement of the outer indication element 17 to bring the second detents 22 out of engagement with the counter element 24 is minimized or even prevented. Hence, the indicator 13 is effectively prevented from switching from the second indication position back into the first indication position.

Accordingly, the protrusions 26 act for preventing rotation of the indicator 13 in a direction opposite to the delivery direction to unintentionally switch the indicator 13 from the first indication position into the second indication position. However, as the protrusions 26 are ramp-shaped in the delivery direction, proximal displacement of the outer indication element 17 to bring the first detents 21 out of engagement with the counter elements 24 for switching the indicator 13 from the first indication position into the second indication position is not prevented, when the indicator 13 is rotated in the delivery direction.

In the following, the operation of priming the device 1 is described, as shown in FIG. 9:

The user pulls the dose button 12 proximally for setting the prime dose. Proximal movement of the dose button 12 is converted into proximal movement of the drive member 11 with respect to the housing 2. The indicator 13 moves proximally together with the dose button 12 and the drive sleeve 11.

After the prime dose has been set, the user pushes the dose button 12 and, hence, the drive member 11 distally. Thereby, the indicator 13 is moved distally such that the first interaction surface 20 axially overlaps with the flexible arm 32A of the piston rod 8. Distal movement of the drive member 11 is converted into distal and rotational movement of the piston rod 8 in the delivery direction with respect to the housing 2.

The flexible arm 32A abuts the first interaction surface 20 and, thus, rotation of the piston rod 8 is converted into rotation of the indicator 13 in the delivery direction (see arrow 28 in FIG. 9), the ramp of the primed detents 21 thereby raising the outer indication element 17 out of engagement with the counter elements 24, as described previously. The first indication surfaces 17A are rotated out of the apertures 25 and the second indication surface 17B are rotated into the apertures 25.

The outer indication element 17 is biased distally by means of the flexible members 23 and, hence, when the second detents 22 have reached the counter elements 24, the second detents 22 get engaged with the counter elements 24, preventing further rotation of the indicator 13 which would switch the indicator 13 from the second indication position back into the first indication position. Now, the device 1 is in the primed condition and the indicator 13 is irreleasably secured in the second indication position.

Accordingly, the user is indicated that the device 1 has been primed and hence, that the device 1 is ready for setting and dispensing the first dose of the drug 31. When the first dose is set, the first interaction surface 20 disengages with the flexible arm 32A. Hence, mechanical cooperation of the piston rod 8 and the indicator 13 is prevented when the piston rod 8 travels towards the distal end position for dispensing the drug 31. Setting and dispensing a dose of the drug 31 may occur in the same way as described for setting and dispensing the prime dose.

The device 1 described above provides clear visual signals indicating to the user whether the device 1 has been primed or not. As the signal is binary, it is very difficult to misinterpret it. Hence, a user-friendly and easily handled drug delivery device 1 is achieved. Due to the shape of the flexible members 23, the device 1 minimizes the force required for priming the device 1, which is especially useful for users with limited mobility. The above described indicator 13 is an easy to manufacture component and hence, a very cost-effective drug delivery device 1 is achieved.

Other implementations are within the scope of the following claims. Elements of different implementations may be combined to form implementations not specifically described herein.

The invention claimed is:

1. An assembly for a drug delivery device, comprising:
   a housing having a proximal end and a distal end,
   a piston rod which is adapted to be displaced distally with respect to the housing away from a proximal start position and towards a distal end position for delivering a drug,
   an indicator for indicating at least two different operation conditions of the assembly, the indicator comprising a first detent and a second detent, the indicator being moveable with respect to the housing from a first indication position for a first condition of the assembly into a second indication position for a second condition of the assembly, wherein
   the piston rod and the indicator are configured to mechanically interact for converting rotational movement of the piston rod into rotational movement of the indicator, and wherein
   the first detent is configured to releasably secure the indicator in the first indication position such that movement into the second indication position is allowed, and
   the second detent is configured to secure the indicator in the second indication position such that movement into the first indication position is prevented.

2. The assembly according to claim 1, wherein the second detent irreleasably secures the indicator in the second indication position while the piston rod travels to the distal end position.

3. The assembly according to claim 1, wherein the piston rod is rotatable in a first rotational direction with respect to the housing and, wherein, the indicator is arranged and configured to mechanically interact with the piston rod such that the indicator is at least partly rotated together with the piston rod in the first rotational direction when the assembly switches from the first indication position into the second indication position.

4. The assembly according to claim 3, wherein the first detent comprises a ramp for releasably securing the indicator in the first indication position, and, wherein, the ramp rises in the first rotational direction.

5. The assembly according to claim 1, comprising a drive member and a dose button, wherein the dose button is moveable with respect to the housing, with movement of the dose button being converted into movement of the drive member by mechanical interaction of dose button and drive member, wherein movement of the dose button in the distal direction with respect to the housing causes transition of the indicator from the first indication position into the second indication position.

6. The assembly according to claim 5, comprising at least one counter element for engaging the respective detent, wherein the at least one counter element is part of the drive member and, wherein, when the counter element engages with one of the detents, the counter element is disengaged from the other one of the detents.

7. The assembly according to claim 1, wherein the indicator comprises an inner member and an outer indication element, the inner member and the outer indication element being resiliently connected with each other such that the outer indication element is moveable with respect to the inner member when switching from the first indication position into the second indication position.

8. The assembly of claim 7 wherein the inner member is configured to cooperate with the piston rod for switching from the first indication position into the second indication position and, wherein, the inner member comprises at least one first interaction surface, wherein movement of the piston rod is converted into movement of the indicator by mechanical cooperation of the first interaction surface and the piston rod.

9. The assembly of claim 8, wherein the inner member comprises at least one second interaction surface, with mechanical cooperation of the second interaction surface and the piston rod keeping the indicator in the first indication position.

10. The assembly of claim 9, wherein the first interaction surface protrudes radially outwardly from the inner member and the second interaction surface is arranged closer to a proximal end of the piston rod than the first interaction surface, and, wherein an angular distance between the second interaction surface and the piston rod is smaller than an angular distance between the first interaction surface and the piston rod.

11. The assembly according to claim 7, wherein the inner member and the outer indication element are connected by means of at least one flexible member and, wherein, when the first detent and the second detent are disengaged from a counter element, the flexible member provides a force which tends to displace the indicator element in the distal direction with respect to the housing.

12. The assembly according to claim 11, wherein the flexible member is secured to an end face of the outer indication element, the flexible member running in the radial direction with respect to the housing and, wherein the flexible member is shaped s-like.

13. The assembly according to claim 11, wherein the dose button comprises a plurality of protrusions arranged on an inner surface of the dose button, the protrusions being configured to mechanically interact with the at least one flexible member such that movement of the indicator away from the second indication position and back towards the first indication position is prevented.

14. The assembly according to claim 1, wherein the indicator is configured to be a prime status indicator and, wherein, the first indication position denotes an unprimed condition of the assembly and, wherein the second indication position denotes a primed condition of the assembly.

15. An indicator for a drug delivery device, the indicator comprising an inner member and an outer indication element, the outer indication element providing an indication surface and being resiliently connected to the inner member by at least one flexible member, wherein the indicator comprises at least one first detent and at least one second detent, the first detent being adapted to enable rotation of the indicator in a first direction and the second detent being adapted to prevent rotation of the indicator in the direction opposite to the first direction, and wherein the indicator is rotatable via mechanical engagement with a piston rod of the drug delivery device.

16. An assembly for a drug delivery device, comprising:
a housing having a proximal end and a distal end,
a piston rod which is adapted to be displaced distally with respect to the housing away from a proximal start position and towards a distal end position for delivering a drug,
an indicator for indicating at least two different operation conditions of the assembly, the indicator being moveable with respect to the housing from a first indication position for a first condition of the assembly into a second indication position for a second condition of the assembly, the indicator comprising an inner member and an outer indication element, the inner member and the outer indication element being resiliently connected with each other such that the outer indication element is moveable with respect to the inner member when switching from the first indication position into the second indication position, wherein
the piston rod and the indicator are configured to mechanically interact for converting rotational movement of the piston rod into rotational movement of the indicator, and wherein
a first detent is provided which is configured to releasably secure the indicator in the first indication position such that movement into the second indication position is allowed, and
a second detent is provided which is configured to secure the indicator in the second indication position such that movement into the first indication position is prevented.

* * * * *